US00PP33914P2

(12) United States Plant Patent
van Langen

(10) Patent No.: US PP33,914 P2
(45) Date of Patent: Jan. 25, 2022

(54) *ECHEVERIA* PLANT NAMED 'AMIECH2006'

(50) Latin Name: ***Echeveria* hybrid**
Varietal Denomination: AMIECH2006

(71) Applicant: Novoami B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 17/300,673

(22) Filed: Sep. 21, 2021

(30) Foreign Application Priority Data

Nov. 19, 2020 (QZ) ..... PBR 2020/2914

(51) Int. Cl.
*A01H 5/02* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
CPC ..... A01H 6/32; A01H 5/02
See application file for complete search history.

*Primary Examiner* — Keith O. Robinson
(74) *Attorney, Agent, or Firm* — Samuel R. McCoy, Jr.

(57) ABSTRACT

A new and distinct *Echeveria* hybrid plant named 'AMIECH2006' which is characterized by a relative abundance of small, slightly concaved foliage that is arranged in a compact basal rosette, green foliage that is covered with greyed-green epicuticular wax, mature foliage that is tipped greyed-red, and the stability of these characteristics from generation to generation.

4 Drawing Sheets

Latin name of the genus and species: The Latin name of the genus and species of the novel variety disclosed herein is *Echeveria* hybrid.

Variety denomination: The inventive variety of *Echeveria* hybrid disclosed herein has been given the variety denomination 'AMIECH2006'.

CROSS REFERENCE TO RELATED APPLICATIONS

This application claims priority to the Community Plant Variety Rights application number 2020/2914, filed Nov. 19, 2020, which is herein incorporated by reference.

BACKGROUND OF THE INVENTION

Parentage: 'AMIECH2006' is an interspecific hybrid seedling selection resulting from the controlled pollination of an *Echeveria elegans* 'Rose' plant (not patented), the seed parent, with an *Echeveria* hybrid 'Slamrock' plant (not patented), the pollen parent. The crossing was made by the inventor in the summer of 2016 at a commercial greenhouse in Heerhugowaard, the Netherlands. In the autumn of 2017, one seedling was observed which exhibited unique growth and foliage characteristics. The seedling was isolated for further evaluation in order to confirm the distinctness and stability of the characteristics first observed. Upon confirmation of distinctness and stability, 'AMIECH2006' was selected for commercialization.

Asexual Reproduction: Asexual reproduction of the new cultivar 'AMIECH2006', by way of rooting leaf cuttings, was first initiated in the spring of 2018 at the inventor's commercial greenhouse in Heerhugowaard, the Netherlands.

Through five subsequent generations, the unique features of this cultivar have proven to be stable and true to type.

SUMMARY OF THE INVENTION

The cultivar 'AMIECH2006' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH2006'. These characteristics in combination distinguish 'AMIECH2006' as a new and distinct *Echeveria* hybrid cultivar:

1. 'AMIECH2006' exhibits an abundance of relatively small foliage arranged in a compact basal; and
2. 'AMIECH2006' exhibits slightly concaved, obovate to broadly oblanceolate foliage; and
3. 'AMIECH2006' exhibits green juvenile foliage that is narrowly margined with a translucent yellow-green and moderately covered with greyed-green epicuticular wax; and
4. 'AMIECH2006' exhibits green mature foliage is narrowly margined with greyed-green and moderately covered with greyed-green epicuticular wax tipped with greyed-red.
5. 'AMIECH2006' exhibits mature foliage that is tipped with greyed-red.

BOTANICAL DESCRIPTION OF THE PLANT

Figure 1:
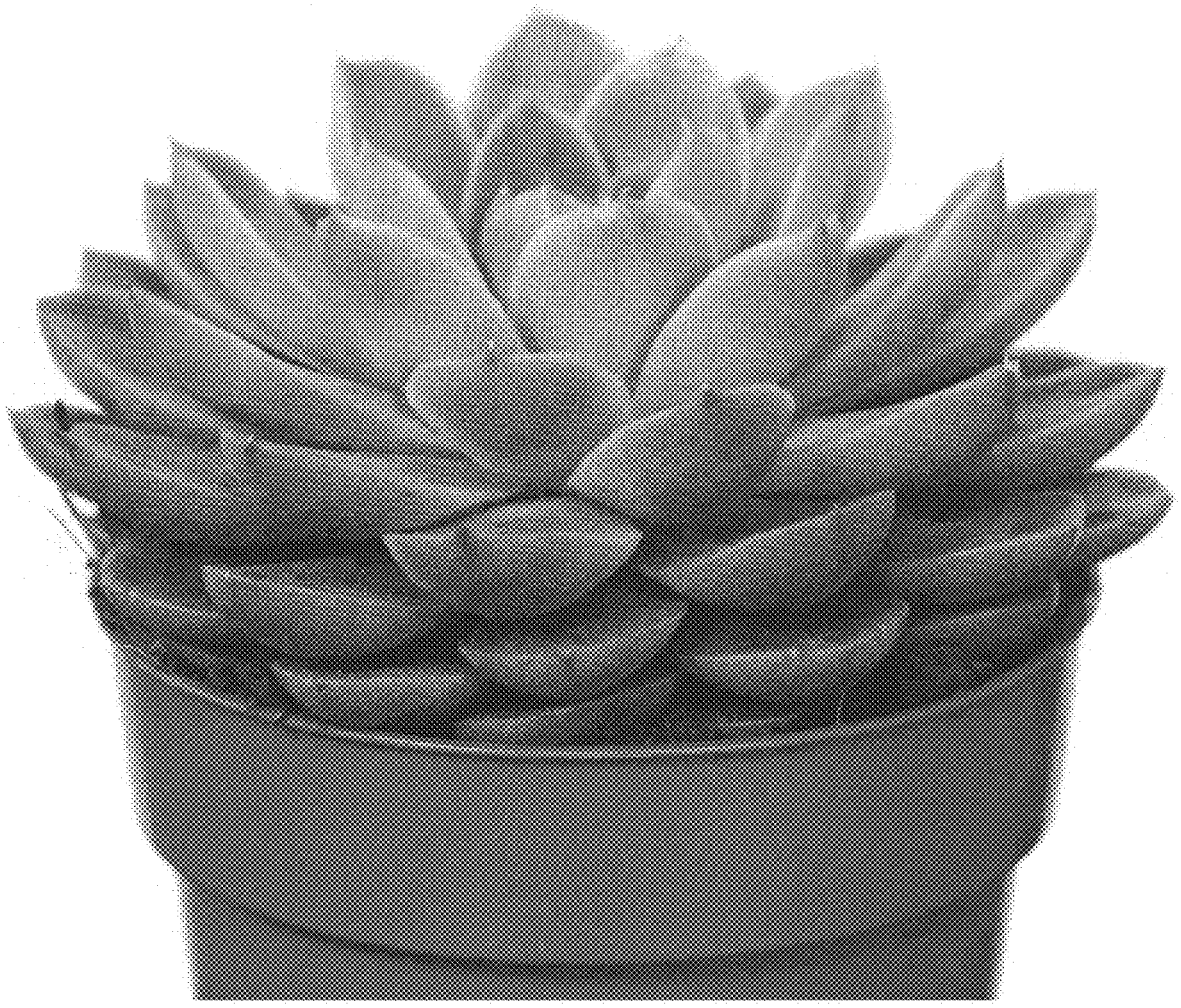
FIG. 1 illustrates, as nearly true as it is reasonably possible to make the same in color photographs of this type, an exemplary plant of 'AMIECH2006' grown in a commercial greenhouse in Heerhugowaard, the Netherlands. This plant is approximately 25 week-old, shown planted in an 8.5 cm container.
Figure 2:
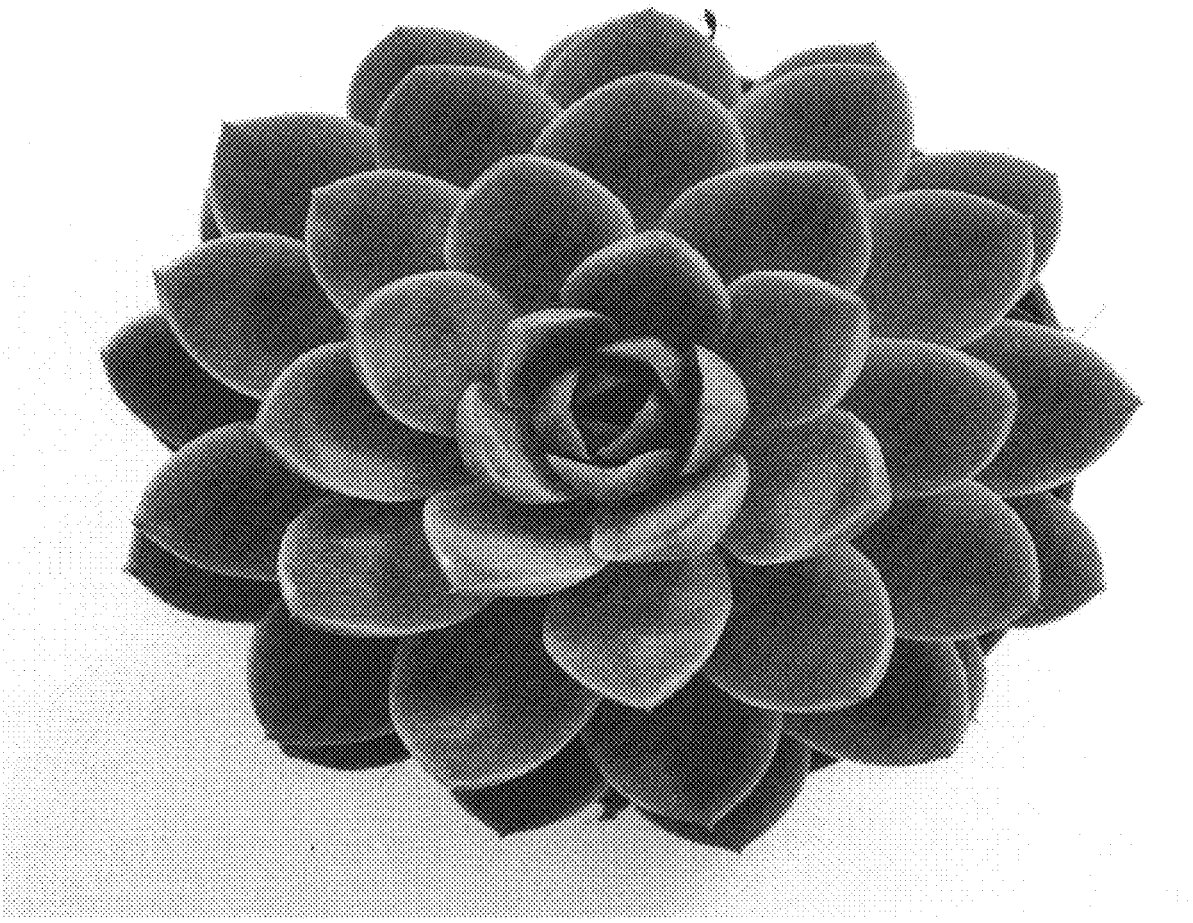
FIG. 2 illustrates, as nearly true as it is reasonably possible to make the same in color photographs of this type, the typical foliage arrangement of 'AMIECH2006'.
Figure 3:
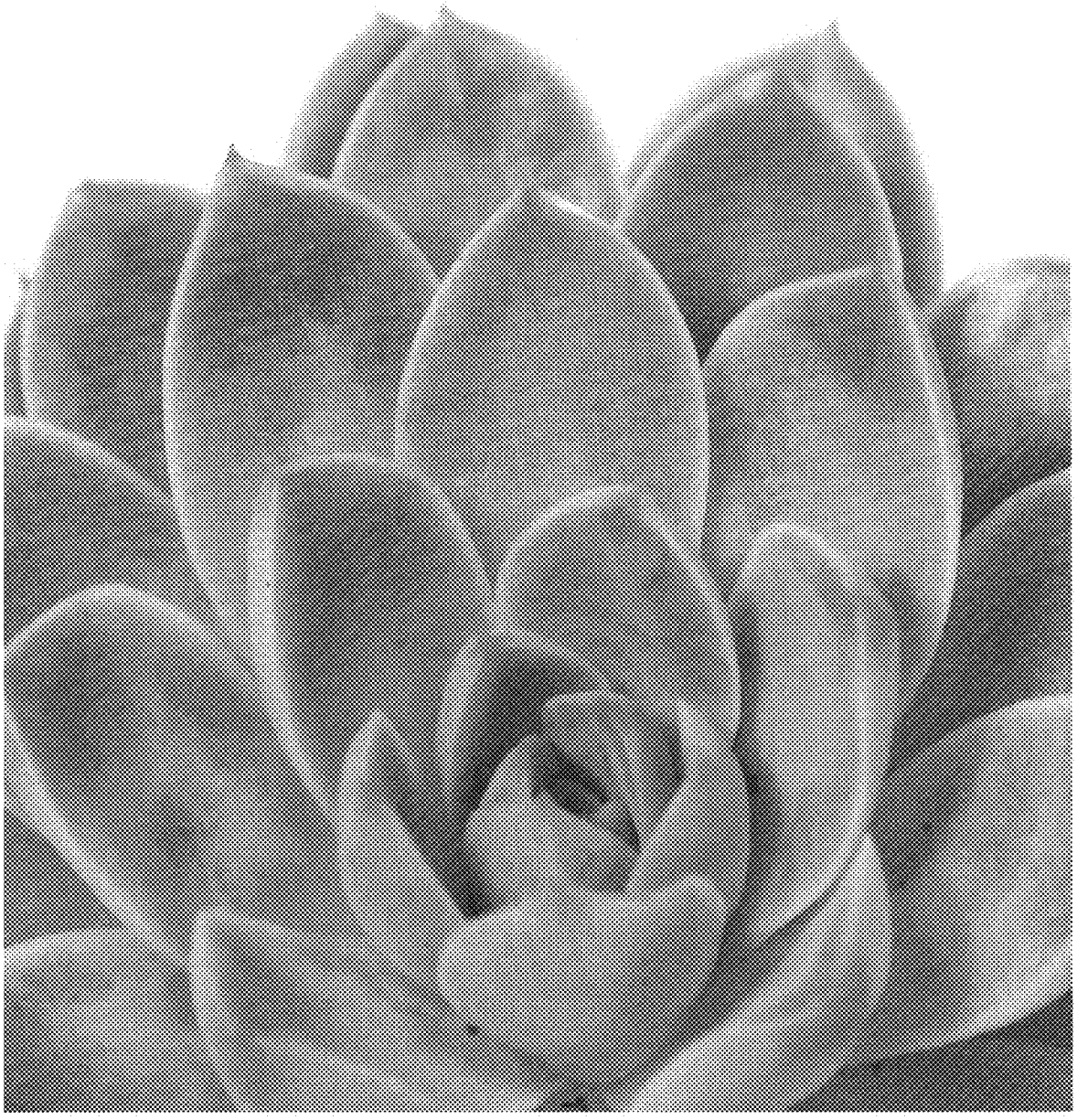
FIG. 3 illustrates, as nearly true as it is reasonably possible to make the same in color photographs of this type, the adaxial surface of the mature foliage 'AMIECH2006'.
Figure 4:
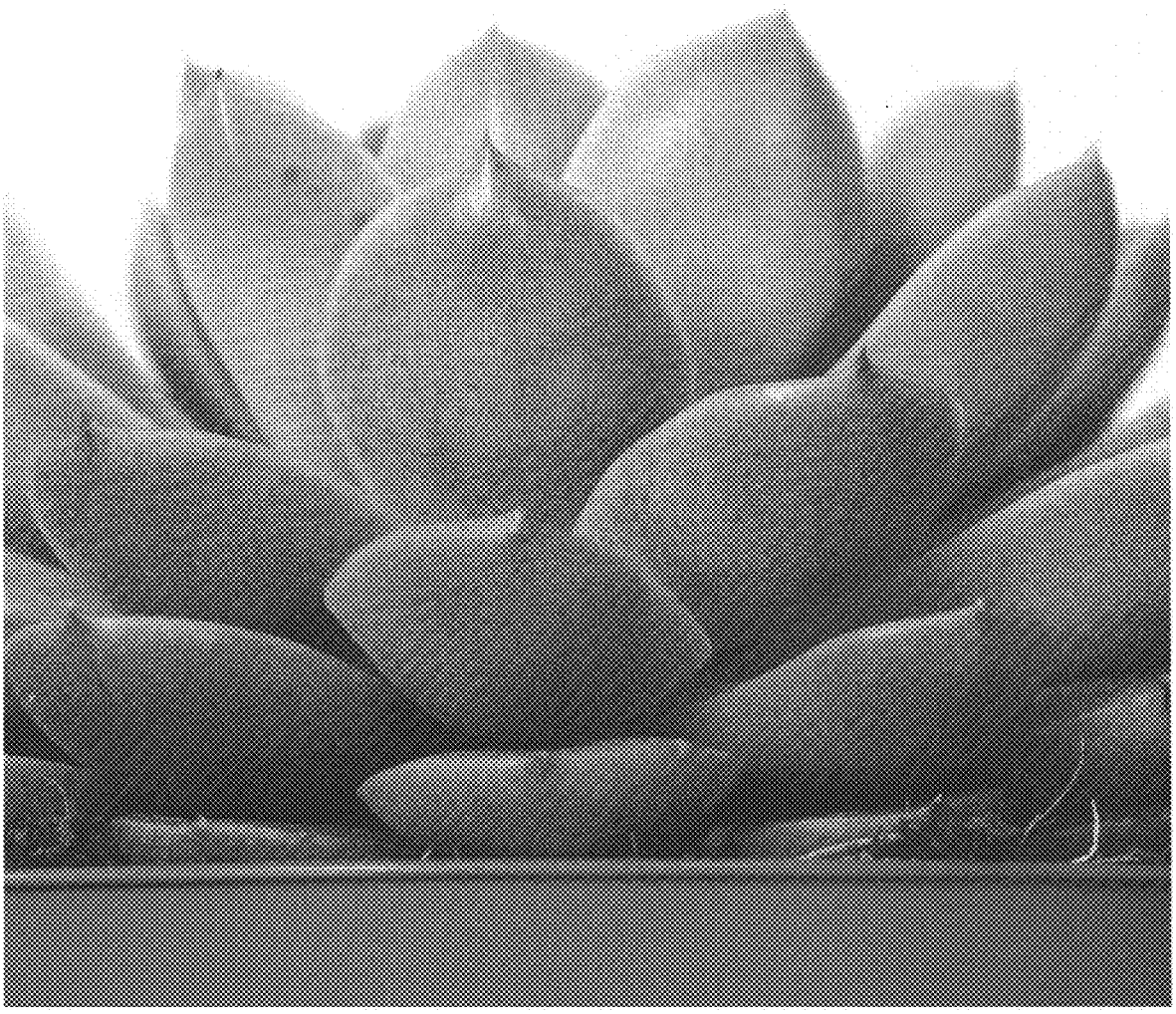
FIG. 4 illustrates, as nearly true as it is reasonably possible to make the same in color photographs of this type, the abaxial surface of the mature foliage 'AMIECH2006'.

The following observations and measurements made in June of 2021 describe averages from a sample set of six specimens of 25 week-old 'AMIECH2006' plants grown in 8.5 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH2006' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'AMIECH2006' and comparisons with the parent plants and closest known comparator are provided below.

Plant description:

*Growth habit*.—Succulent perennial with foliage growing in a non-branched basal rosette.

*Plant shape*.—Flattened globular.

*Height from soil level to top of foliar plane*.—4.8 cm.

*Plant spread*.—Average of 10.0 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 25 weeks to produce a marketable plant in an 8.5 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 58 leaves per rosette.

*Shape*.—Obovate to broadly oblanceolate.

*Dimensions*.—4.2 cm long, 1.9 cm wide, and 0.65 cm thick, on average.

*Aspect*.—Slightly concave.

*Attitude*.—Juvenile foliage at the center of the rosette is held upright; foliage becomes progressively more relaxed towards the outer whorls of mature foliage; mature foliage is held at approximately 30 degrees to horizontal.

*Apex*.—Mucronate.

*Base*.—Cuneate.

*Margin*.—Entire; margins are not undulate.

*Pubescence, texture and luster of the adaxial surface*.—Smooth, glabrous, and moderately glaucous.

*Pubescence, texture and luster of the abaxial surface*.—Smooth, glabrous, and moderately glaucous.

*Luster of the adaxial surface*.—Slightly glossy.

*Luster of the abaxial surface*.—Moderately glossy.

*Color*.—Juvenile foliage, adaxial surface — Green, nearest to RHS 137C, and narrowly margined with a translucent yellow-green, nearest to RHS 146D; tipped greyed-green, nearest to RHS 193B. The epicuticular glaucous wax covering the leaf surface is greyed-green, nearest to RHS 188A. Juvenile foliage, abaxial surface — Green, nearest to RHS 138B, and narrowly margined with a translucent yellow-green, nearest to RHS 146D; tipped greyed-green, nearest to RHS 193B. The epicuticular glaucous wax covering the leaf surface is greyed-green, nearest to RHS 188C. Mature foliage, adaxial surface — Green, nearest to RHS NN137B, and fading to yellow-green towards the base, nearest to RHS 147C; narrowly margined greyed-green, nearest to RHS 193A and nearest to RHS 193B towards the base; tipped greyed-red, nearest to RHS 182C. The epicuticular glaucous wax covering the leaf surface is greyed-green, nearest to RHS 188A. Mature foliage, abaxial surface — Nearest to a mixture of green and yellow-green, RHS 138B and 147B; fading to yellow-green towards the base, nearest to RHS 148D; narrowly margined with greyed-green, nearest to RHS 193A and nearest to RHS 193B towards the base; tipped with greyed- red, nearest to RHS 182C. The epicuticular glaucous wax covering the leaf surface is greyed-green, nearest to RHS 188C. Venation, adaxial surface — No visible venation. Venation, abaxial surface — No visible venation.

*Petiole*.—No petiole; leaves are sessile.

Inflorescence: No flowering has been observed to date.

COMPARISONS WITH THE PARENT PLANTS AND CLOSEST KNOWN COMPARATOR

Plants of the new cultivar 'AMIECH2006' differ from the seed parent, *Echeveria elegans* 'Rose' (not patented), in the following characteristics described in Table 1 below.

TABLE 1

| Characteristic | 'AMIECH2006' | 'Rose' |
|---|---|---|
| Foliage apex. | More pointed than 'Rose'. | More rounded than 'AMIECH2006'. |
| General coloration of the foliage. | Green and covered with a layer of greyed-green epicuticular wax; mature foliage is tipped greyed-red. | Light green and covered with greyed-purple epicuticular wax which gives the foliage a light blue-green appearance. |

Plants of the new cultivar 'AMIECH2006' differ from the pollen parent, *Echeveria* hybrid 'Slamrock' (not patented), in the following characteristics described in Table 2 below.

TABLE 2

| Characteristic | 'AMIECH2006' | 'Slamrock' |
|---|---|---|
| General coloration of the foliage. | Green and covered with a layer of greyed-green epicuticular wax; mature foliage is tipped greyed-red. | Green and suffused with greyed-red. |

COMPARISONS WITH THE CLOSEST KNOWN COMPARATOR

Plants of the new cultivar 'AMIECH2006' differ from the closest known commercial comparator, *Echeveria* hybrid 'Green Gilva' (not patented), in the following characteristics described in Table 3 below.

TABLE 3

| Characteristic | 'AMIECH2006' | 'Green Gilva' |
|---|---|---|
| Plant size. | Larger than 'Green Gilva'. | Smaller than 'AMIECH2006'. |
| Foliage aspect. | Slightly concaved. | Flat. |
| General coloration of the mature foliage. | Green and narrowly margined greyed-green; moderately glaucous, with greyed-green epicuticular wax; tipped greyed-red. | Green and narrowly margined with greyed-red; strongly glaucous, with greyed-green epicuticular wax that gives the foliage a light greyed-green appearance; tipped greyed-red. |

That which is claimed is:

1. A new and distinct variety of *Echeveria* hybrid plant named 'AMIECH2006', substantially as described and illustrated herein.

* * * * *